United States Patent [19]

Kawata et al.

[11] Patent Number: 5,563,411
[45] Date of Patent: *Oct. 8, 1996

[54] SCANNING PHOTOELECTRON MICROSCOPE

[75] Inventors: Shintaro Kawata, Kawasaki; Keitaro Hara, Ichikawa, both of Japan

[73] Assignee: Nikon Corporation, Tokyo, Japan

[*] Notice: The term of this patent shall not extend beyond the expiration date of Pat. No. 5,446,282.

[21] Appl. No.: 451,052

[22] Filed: May 25, 1995

Related U.S. Application Data

[63] Continuation of Ser. No. 220,173, Mar. 30, 1994, Pat. No. 5,446,282.

[30] Foreign Application Priority Data

Apr. 5, 1993 [JP] Japan ................................. 5-77924
Jan. 26, 1994 [JP] Japan ................................. 6-6824

[51] Int. Cl.⁶ ........................................... G01N 23/22
[52] U.S. Cl. ................................. 250/306; 250/305
[58] Field of Search ................................. 250/305, 306, 250/423 P; 378/43

[56] References Cited

U.S. PATENT DOCUMENTS

| | | | |
|---|---|---|---|
| 4,785,182 | 11/1988 | Mancuso | 250/310 |
| 4,912,737 | 3/1990 | Ohsuka et al. | 378/43 |
| 5,045,696 | 9/1991 | Hirose | 250/306 |
| 5,119,411 | 6/1992 | Nakamura | 378/43 |
| 5,138,158 | 8/1992 | Ninomiya et al. | 250/305 |
| 5,393,980 | 2/1995 | Yost et al. | 250/306 |

*Primary Examiner*—Bruce C. Anderson
*Attorney, Agent, or Firm*—Shapiro and Shapiro

[57] ABSTRACT

A scanning photoelectron microscope comprises a stage on which a sample is placed in a state in which gas around the sample is present, a light source emitting light of a wavelength capable of causing photoelectrons to be emitted from the sample, an optical system for condensing the light from the light source on the sample, scanning means for scanning the sample and the light relative to each other, and detecting means capable of applying positive potential to the sample, and detecting the photoelectrons created from the sample by the condensing, through the gas.

20 Claims, 5 Drawing Sheets

SCANNING PHOTOELECTRON MICROSCOPE

This is a continuation of application Ser. No. 08/220,173 filed Mar. 30, 1994 U.S. Pat. No. 5,446,282.

BACKGROUND OF THE INVENTION

1. Field of the Invention

This invention relates to a scanning photoelectron microscope, and particularly to a scanning photoelectron microscope for observing therethrough a sample having much gas emission, a sample containing water, etc.

2. Related Background Art

In recent years, attention has been paid to a scanning photoelectron microscope as an apparatus for observing therethrough the chemically coupled state of the surface of a sample.

The scanning photoelectron microscope has scanned a sample placed in a vacuum state higher than $10^{-1}$ Pa with an energy beam (such as X-rays or ultraviolet rays), has processed photoelectrons created from the sample by this scanning in the following manner and has displayed the result on a CRT.

That is, the photoelectrons created from the sample have been detected by a detector comprising a combination of a microchannel plate or a scintillator and a photoelectronic multiplier tube.

The photoelectrons detected by the detector have been stored as an image signal in an image memory in synchronism with the aforementioned scanning, and have been displayed on the CRT.

Also, when it is desired to observe photoelectrons having desired energy, an electron energy analyzer has been disposed between the sample and the detector, and only the photoelectrons having desired energy have been taken out by this electron energy analyzer, whereafter the photoelectrons having desired energy have been detected by the detector.

By the prior-art detector, however, the photoelectrons created from the sample can be detected only in the aforementioned high vacuum state, and this has led to a problem that a sample having much gas emission and a sample containing water cannot be observed.

SUMMARY OF THE INVENTION

So, the present invention has as its object the provision of a scanning photoelectron microscope capable of detecting even photoelectrons from a sample having much gas emission or a sample containing water.

The present invention includes a stage on which a sample is placed in a state in which gas around the sample is present, a light source emitting light of a wavelength capable of causing photoelectrons to be emitted from said sample, an optical system for condensing the light from said light source on said sample, scanning means for scanning said sample and said light relative to each other, and detecting means capable of imparting positive potential to said sample, and detecting photoelectrons created from said sample by said condensing, through said gas.

A preferred embodiment of the present invention further includes a sample chamber for containing said sample and said detecting means therein and keeping them air-tight to the surroundings, a window for introducing said light into said sample chamber, and control means for controlling said sample chamber to a gas atmosphere of predetermined pressure.

Also, the present invention includes a stage on which a sample is placed in a state in which gas around the sample is present, a light source emitting light of a wavelength capable of causing photoelectrons to be emitted from said sample, an optical system for condensing the light from said light source on said sample, scanning means for scanning said sample and said light relative to each other, electron energy selecting means for selecting only those of the photoelectrons created from said sample which have predetermined energy, detecting means capable of imparting positive potential to said sample, and detecting the photoelectrons selected by said electron energy selecting means, through said gas, and a sample chamber capable of containing said sample, said electron energy selecting means and said detecting means therein so as to keep them air-tight to the surroundings, and introducing said light into said sample.

According to a preferred embodiment, when the ionization cross section of said gas by electrons is G and the molecule number density of said gas is N, said electron energy selecting means is disposed at a location within a value L found by the following equation from said sample toward the optical axis of said condensing optical system:

$$L = 1/(N \cdot \sigma)$$

More preferably, a preferred embodiment of the present invention includes control means for controlling said sample chamber to a gas atmosphere of predetermined pressure.

In the present invention, light (an electromagnetic wave of a short wavelength less than a microwave) is applied to the sample in the gas atmosphere, whereby photoelectrons are emitted from the sample. As is well known, photoelectrons are obtained by an electromagnetic wave of a short wavelength less than a microwave, and especially, a wavelength shorter than ultraviolet rays is advantageous. The light from which photoelectrons are obtained is distinguished from corpuscular rays such as electron rays. This photoelectron, which it flies toward a detector (electrode) given positive potential while being accelerated, collides with a gas molecule between the sample and the detector (electrode) and ionizes the molecule. As a result, the electron of the photoelectron is amplified to two. By repeating this step, the electron of the photoelectron is further amplified. This is called the electron multiplying action.

This amplified photoelectron is detected by the detector (electrode) and becomes a photoelectron signal.

The amplification degree of the photoelectron is obtained from Townsend's first coefficient, and depends on the pressure of the gas, the kind of the gas, the potential of the detector and the distance between the sample and the detector. Therefore, the combination of these is determined by the photoelectron signal. For example, the sample is placed in oxygen gas of 1330 Pa (10 Torr), light of a wavelength 254 nm is applied to the sample, and a voltage of about 500 V is applied to the detector spaced apart by about 10 mm from the sample, whereby the photoelectron from the sample can be detected.

Also, when it is desired to observe a photoelectron having desired energy, when the ionization cross section of the gas by an electron is σ and the molecule number density of the gas is N, the electron energy selecting means is disposed at a location within a value L found by the following equation from the sample toward the optical axis of the condensing optical system. The following equation is for finding the distance by which the photoelectron advances its energy without losing (amplifying) the energy.

$$L=1/(N \cdot \sigma)$$

Thereby, without the loss of the energy of the photoelectron created from the sample, this photoelectron can be directed to the electron energy selecting means.

The electron energy selecting means selects only a photoelectron having desired energy. The detecting means detects this selected photoelectron through a gas having the electron multiplying action. Thereby, the photoelectron having desired energy can be detected without the sample chamber being kept in high vacuum and therefore, a sample having much gas emission, a sample containing water, etc. can be observed.

Also, the control means controls the interior of the sample chamber in a gas atmosphere having the electron multiplying action of predetermined pressure. Therefore, the pressure of the sample chamber can be set in accordance with the sample to be observed.

DETAILED DESCRIPTION OF THE PREFERRED EMBODIMENTS

Figure 1:
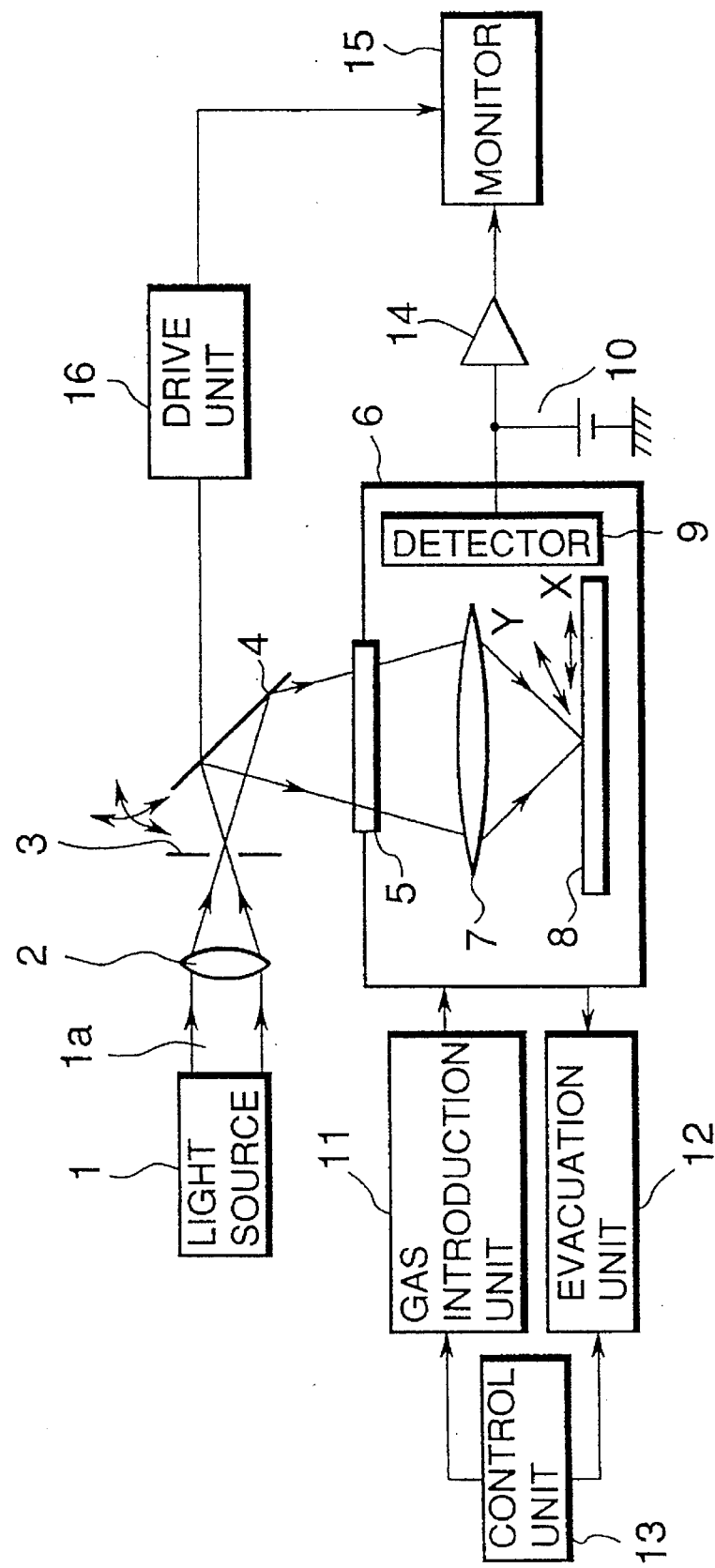
FIG. 1 is a schematic diagram of a scanning photoelectron microscope according to a first embodiment of the present invention.

FIG. 1 is a schematic diagram of an embodiment of a scanning photoelectron microscope according to the present invention.

In FIG. 1, a beam of light 1a from a light source 1 is caused to pass through an aperture 3 by a condenser lens 2, is caused to enter a scanning mirror 4 by a drive unit 16 and is introduced into a sample chamber 6 into which gas has been introduced, by the reflection of the scanning mirror 4 through a window 5. The beam of light introduced into the sample chamber 6 is condensed on a sample on a stage 8 by an objective lens 7.

The beam of light is caused to scan the surface of the sample two-dimensionally (in X-direction and Y-direction) by the scanning mirror 4, as required. Two scanning mirrors 4 for X-direction and Y-direction, respectively, for thus scanning the beam of light are usually prepared, but such construction is well known and therefore, in FIG. 1, for the sake of convenience, only one mirror 4 is shown. For example, of course, X-direction may be scanned by the scanning mirror and in Y-direction, the surface of the sample may be moved, or the surface of the sample may be moved two-dimensionally.

A photoelectron emitted from the sample by the application of the light thereto ionizes the gas in the sample chamber 6, whereby the multiplied electron is captured by a detector 9 (electrode) of positive potential relative to the sample. That is, the detector 9 is maintained at positive potential by a power source 10 (the sample is earthed), and such a distance and voltage that no discharging will take place between the detector and the sample are determined. The sample chamber 6 is kept at predetermined pressure by controlling a gas introduction unit 11 and an evacuation unit 12 by a gas control unit 13.

A photoelectron signal is displayed on a monitor 15 through an amplifier 14 in synchronism with the mirror scanning. With such a construction, the sample interchange door, not shown, of the sample chamber 6 is opened, and then the sample is placed onto the stage 8 and the sample interchange door is closed, whereafter the gas control unit 13 is operated to control the gas introduction unit 11 and the evacuation unit 12, thereby keeping the interior of the sample chamber 6 at predetermined pressure. Thereafter, the light from the light source 1 is emitted (this is accomplished by the changeover from the turn-off to the turn-on of the light source, or by the changeover from the closing to the opening of a shutter, not shown).

The beam of light 1a on the sample is caused to scan two-dimensionally by the drive unit 16, whereby the photoelectron emitted from the sample travels toward the detector 9, but is captured by the detector 9 with an electron created as a result of the photoelectron colliding with the gas to thereby ionize the gas, and is amplified by the amplifier 14, whereafter it is inputted to the monitor 15 and becomes the calescence point signal of the monitor 15, whereby the two-dimensional photoelectron image of the sample is displayed on the monitor 15.

Figure 2:
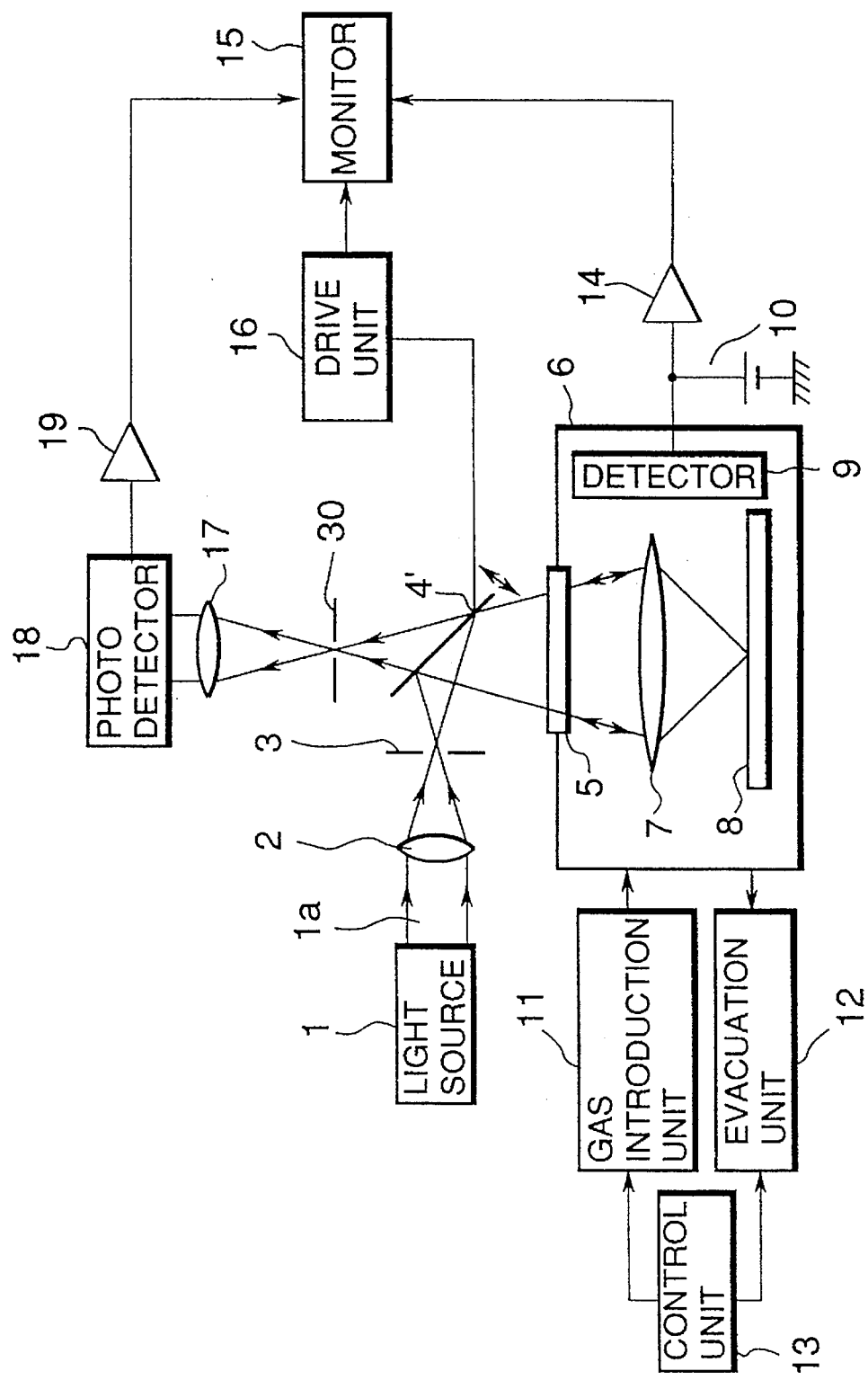
FIG. 2 is a schematic diagram of a combination of a scanning photoelectron microscope according to a modification of the first embodiment and a scanning optical microscope.

FIG. 2 shows a modification comprising a combination of the scanning photoelectron microscope shown in FIG. 1 and a scanning optical microscope, and in FIG. 2, the same members as those in FIG. 1 are given the same reference numerals and need not be described. The scanning mirror 4 in FIG. 1 is constructed as a half-transmitting scanning mirror 4' using a half mirror, and the reflected light from the sample is passed through an aperture 30 and a condenser lens 17 and is detected by a photodetector 18. The detection signal is amplified by an amplifier 19, whereafter it enters the monitor 15 and is displayed as a sample image on the monitor 15 in synchronism with the scanning of the half-transmitting scanning mirror 4'. The outputs of the amplifiers 14 and 19 are superposed one upon the other, whereby an optical image and a photoelectron image are obtained at a time. Of course, the output of the amplifier 14 and the output of the amplifier 19 may be selected by a changeover switch, not shown, which is provided in the monitor 15, and the optical image and the photoelectron image may be alternatively displayed.

Figure 3:
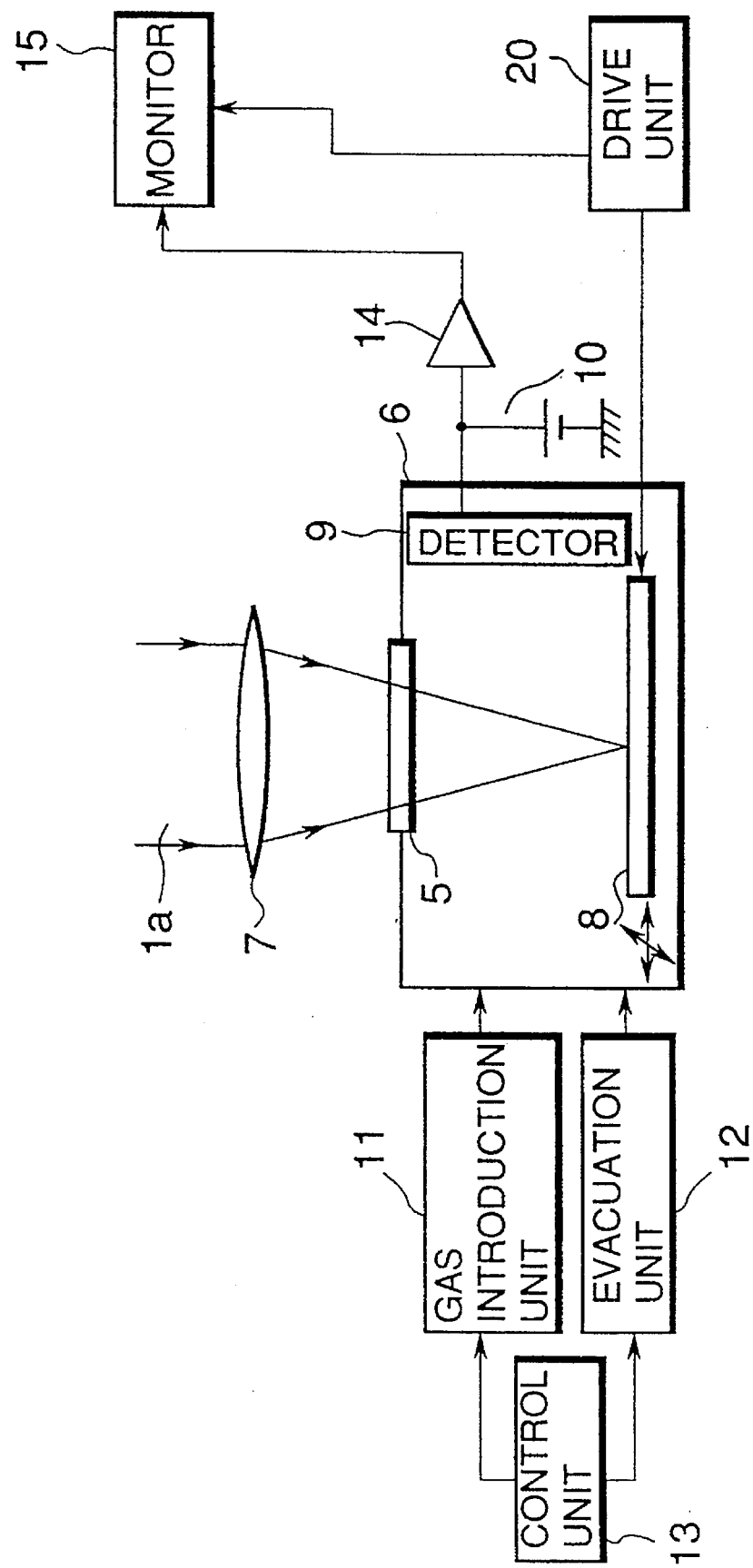
FIG. 3 is a diagram showing a second modification of the first embodiment.

FIG. 3 shows a second modification in which the beam of light 1a is not scanned, but the stage 8 is driven two-dimensionally by a stage drive unit 20 and the sample is scanned relative to the beam of light 1a and the sample is disposed in the atmosphere, the photoelectron signal is captured by the detector 9, is amplified by the amplifier 14 and is displayed on the monitor 15 in synchronism with the scanning of the sample.

In FIG. 3, the beam of light 1a from the light source is a beam of light difficult to scan by a mirror, for example, X-rays from synchrotron radiation or the like, and the mirror 7 is a toroidal X-ray mirror or a Freznel zone plate. A beryllium X-ray window is used as the window 5.

Also, in the above-described embodiments, the sample is placed in the sample chamber 6, but it is known that photoelectrons are also obtained in the atmosphere, and it is not requisite to confine the sample in the pressure-controlled sample chamber 6.

Figure 4:
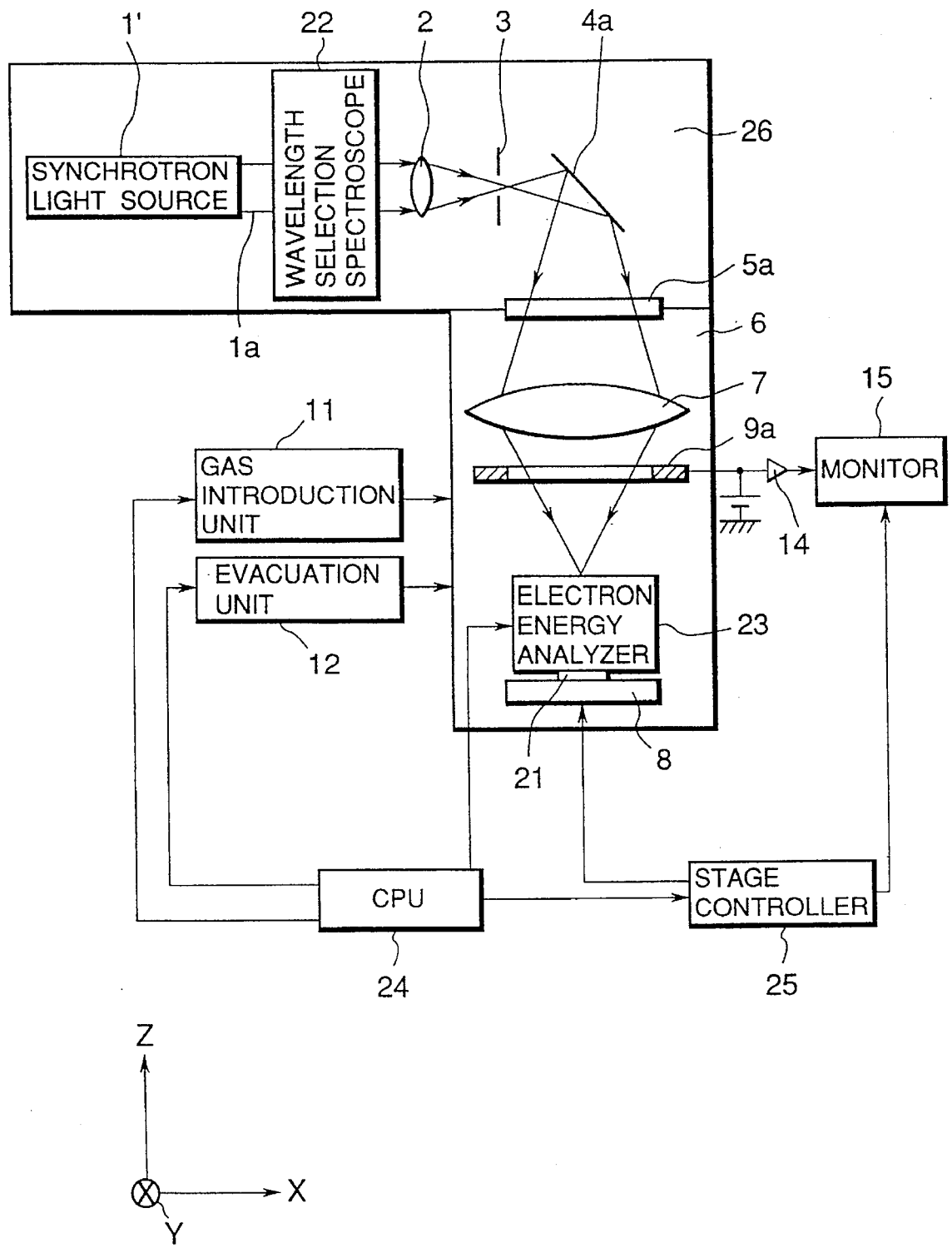
FIG. 4 is a schematic diagram of a scanning photoelectron microscope according to a second embodiment of the present invention.

FIG. 4 is a schematic diagram of a scanning photoelectron microscope according to a second embodiment of the present invention.

In FIG. 4, the same members as those in FIG. 1 are given the same reference numerals and need not be described.

In FIG. 4, a synchrotron light source 1' is a light source capable of emitting lights of wavelengths from the infrared range to the ultraviolet range. A wavelength selection spectroscope 22 selects only the light of necessary wavelength from the beam of light 1a from the synchrotron light source 1' and causes it to enter the condenser lens 2. In the second embodiment, the wavelength selection spectroscope 22 causes only X-rays of wavelength 1 nm to enter the condenser lens 2.

A reflecting mirror 4a reflects the beam of light 1a and causes it to pass through an X-ray transmitting window 5a of thin diamond film, and introduces it into the sample chamber 6 into which gas has been introduced. In the present embodiment, the sample chamber 6 has a volume of 1 m$^3$. Also the arrangement of the optical system takes the absorption of X-rays by the gas into consideration.

The stage 8 is movable two-dimensionally (in X-direction and Y-direction in FIG. 4), and in the second embodiment, by the two-dimensional movement of the stage 8, the beam of light 1a condensed on the sample 21 is caused to scan two-dimensionally on the sample 21.

Photoelectrons created from the sample 21 by this scanning enter an electron energy analyzer 23. The electron energy analyzer 23 passes therethrough only those of photoelectrons created from the sample 21 which have necessary energy, and can be adjusted in Z-direction in FIG. 4 so that it can be disposed at a location whereat the energy of the photoelectrons is not lost (amplified) by the gas atmosphere in the sample chamber 6 (the details of this will be described later). Also, in the present embodiment, an electron energy analyzer of the retarding field type is used as the electron energy analyzer 23.

Figure 5:
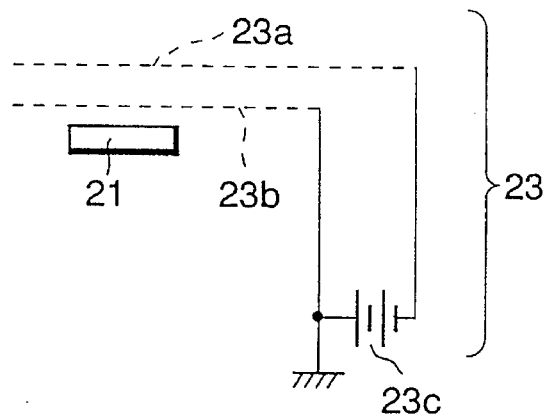
FIG. 5 shows the details of an electron energy analyzer 23.

FIG. 5 shows the details of the electron energy analyzer 23 of FIG. 4, and the electron energy analyzer 23 is comprised of a grid 23a, a grid 23b and a power source 23c. The power source 23c gives a voltage to the grid 23a. The grid 23b drops photoelectrons not enough to satisfy necessary energy to the earth.

Turning back to FIG. 4, the photoelectrons passed through the electron energy analyzer 23 collide with gas molecules in the sample chamber 6, and are detected by a detector 9a which is at positive potential relative to the sample 21. The detector 9a uses a ring-like metal (in the present embodiment, copper) and is disposed so as not to intercept the beam of light 1a, and is given a voltage so that the potential difference thereof from the grid 23a may not exceed 400 V.

A CPU 24 effects the adjustment of the electron energy analyzer 23 in Z-direction through a motor, not shown, and controls the gas introduction unit 11, the evacuation unit 12 and a stage controller 25.

The evacuation unit 12 evacuates the sample chamber 6. The gas introduction unit 11 introduces gas into the sample chamber 6, and in this second embodiment it introduces helium (He).

The stage controller 25 moves the stage 8 two-dimensionally through a motor, not shown, as previously described.

In the second embodiment, X-rays of wavelength 1 nm is used and therefore, the synchrotron light source 1' to the reflecting mirror 4a are covered with a cover 26 of lead.

The observing operation of the scanning photoelectron microscope constructed as described above will hereinafter be described.

Figure 6:
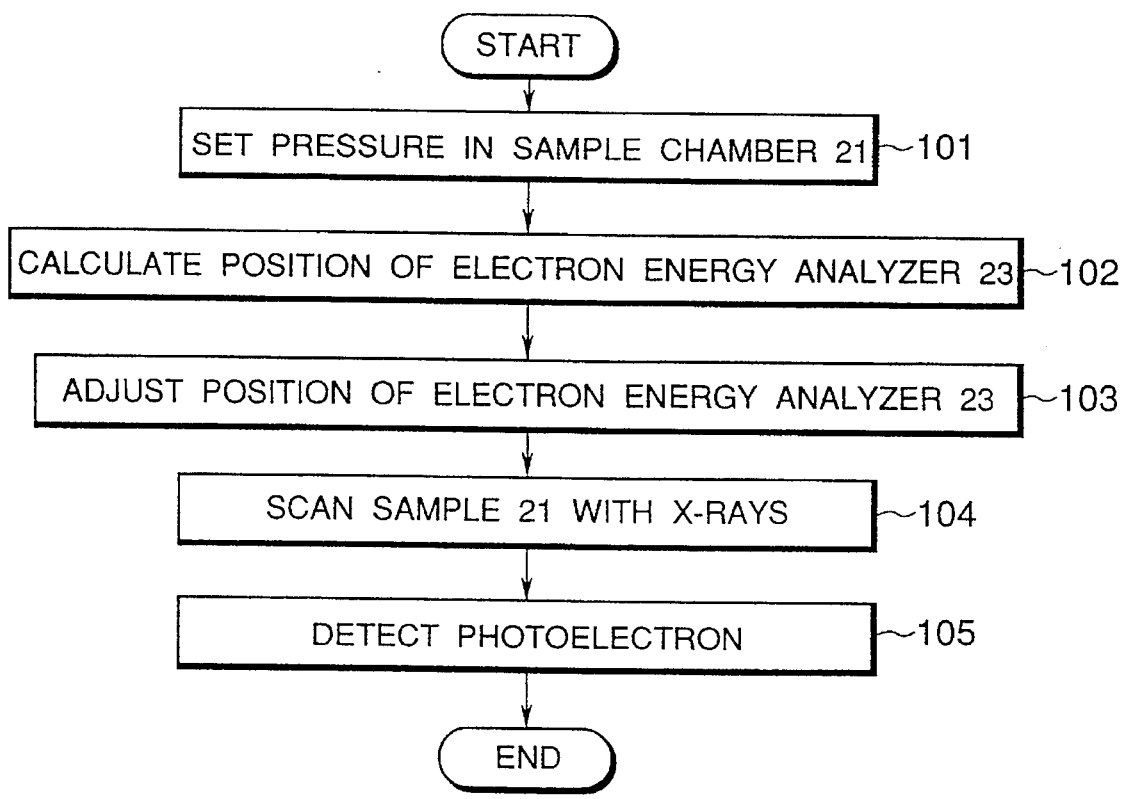
FIG. 6 is a flow chart of a CPU 24.

FIG. 6 is a flow chart for the observation of the sample 21, and description will hereinafter be continued with reference to this flow chart.

The CPU 24 controls the pressure in the sample chamber 6 to the pressure indicated by the operator (step 101).

For example, when the sample chamber 6 is to be set to 500 Pa, the CPU 24 evacuates the sample chamber 6 rendered into the atmospheric pressure by the interchange of the sample 21 to the order of 100 Pa by the evacuation unit 12. The CPU 24 introduces helium by the gas introduction unit 11 until the pressure in the sample chamber 6 becomes 500 Pa. Thereby, the CPU 24 can render the interior of the sample chamber 6 into a helium atmosphere of 500 Pa.

The CPU 24 calculates the position of the electron energy analyzer 23 on the basis of the set pressure (step 102).

The CPU 24 first finds the molecule number density (number/m$^3$) of the helium (He) gas.

The state equation of the gas is expressed by the following equation:

$$P \cdot V = nkt,$$

where P is the pressure (Pa), V is the volume (m$^3$) of the sample chamber 6, n is the molecule number of the gas in the sample chamber 6, is Boltzman's constant (JK$^{-1}$), and T is temperature (K).

Since the molecule number density N (number/m$^3$) is n/V, the above equation can be modified as follows. (The molecule number density of the gas does not depend on the kind of the gas.)

$$N = n/V = P/kT$$

If the temperature in the sample chamber 6 is 300 K (27° C.), as previously described, the volume of the sample chamber 6 is 1 m$^3$ and Boltzman's constant is 1.380662×10$^{-23}$ (JK$^{-1}$) and therefore, these numerical values are substituted for the above equation to thereby calculate $$N = 500/(300 \times 1.380662 \times 10^{-23})$$

and find $$N = 1.207 \times 10^{23} \text{ (number/m}^3\text{)}.$$

The CPU 24 then calculates the position of the electron energy analyzer 23 from the equation below. The equation below is for finding the distance by which the photoelectron advances its energy without losing (amplifying) the energy.

$$L = 1/(N \cdot \sigma),$$

where σ is the ionization and excitation cross section (m$^2$) of the gas by the electron, and when the gas is helium gas in the required photoelectron energy area, σ is 3.6×10$^{-21}$ (m$^2$) at maximum and therefore, $$L = 1/(1.207 \times 10^{23} \times 3.6 \times 10^{-21})$$

is calculated to thereby find $$L = 0.0023 \text{ (}m\text{)} = 2.3 \text{ (}mm\text{)}.$$

The CPU 24 adjusts the position of the electron energy analyzer 23 in the direction of the optical axis (step 103).

The CPU 24 adjusts the grid 23a of the electron energy analyzer 23 so as to assume a position spaced apart by 2.3 (mm) from the sample 21 along the optical axis (Z-direction). The grid 23b is adjusted so as to not to contact with the sample 21.

The CPU 24 moves the stage 8 two-dimensionally and scans the sample 21 with X-rays (step 104).

The wavelength selection spectroscope 22 passes therethough only X-rays of wavelength 1 nm of the beam of light 1a emitted from the synchrotron light source 1' and therefore, the X-rays of wavelength 1 nm are condensed on the sample 21.

When the X-rays are condensed on the sample 21, the CPU 24 moves the stage 8 two-dimensionally through the stage controller 25. By the two-dimensional movement of the stage 8, the sample 21 is scanned with the beam of light 1a (step 105). A photoelectron corresponding to this scanning position is created from the sample 21.

The CPU 24 makes the detector 9a detect the photoelectron created from the sample 21 (step 106).

The grid 23a of the electron energy analyzer 23, as previously described, is at a location spaced apart by 2.3 (mm) from the sample 21 along the optical axis (Z-direction). Therefore, the photoelectrons created from the sample 21 enter the electron energy analyzer 23 without losing (amplifying) their energy. The electron energy analyzer 23 selects and passes therethrough only those of the photoelectrons which have necessary energy. In the second embodiment, an electron energy analyzer of the retarding field type is used as the electron energy analyzer 23 and thus, when as described above, the grid 23a is at a location spaced apart by 2.3 (mm) from the sample 21, a voltage of the order of −400 V is applied with a discharge voltage taken into account.

The photoelectrons passed through the electron energy analyzer 23 collide with the molecules of helium in the sample chamber 6 and the thereby amplified. These photoelectrons are detected by the detector 9a.

The CPU 24 makes the amplifier 14 amplify the photoelectrons detected by the detector 9a as previously described, and causes them to be inputted as an image signal to the monitor 15. Thus, the monitor 15 displays the photoelectron image of the sample 21.

Also, when it is desired to change the pressure in the sample chamber 6 and the kind of the gas, return can be made to the step 101. In the second embodiment, the photoelectrons are amplified by helium, any gas such as steam or nitrogen can be applied.

In the following, the position of the electron energy analyzer 23 when nitrogen ($N_2$) is used as a modification of the second embodiment is found. In this modification, the pressure in the sample chamber 6 is 100 Pa. From the aforementioned state equation of the gas, the molecule density number N when the pressure in the sample chamber 6 is 100 Pa is $N=2.41\times10^{22}$ (number/$m^3$). The maximum value of the ionization and excitation cross section $\sigma$ of nitrogen ($N_2$) by photoelectron is $$\sigma=2.6\times10^{-20} \ (m^2)$$

and therefore, this is substituted for $L=1/(N\cdot\sigma)$ to thereby calculate $$L=1/(2.41\times10^{22}\times2.6\times10^{-20}),$$

thus finding $$L\approx1.60 \ (mm).$$

From this, the grid 23a can be adjusted to a location distant by 1.60 (mm) from the sample 21.

In the present embodiment, X-rays of wavelength 1 nm is used as the light source, but X-rays of other wavelength or ultraviolet rays of a wavelength of the order of 200 nm may also be used.

Also, in the present embodiment the stage 8 is moved two-dimensionally to thereby scan the beam of light 1a condensed on the sample 21 and the sample 21, but alternatively, the reflecting mirror 4a may be caused to scan two-dimensionally. That is, as is well known, two mirrors for X-direction and Y-direction, respectively, can be used and design can be made such that the respective mirrors are caused to scan.

Also, where the sample 21 is electrically conductive, photoelectrons not enough to satisfy the necessary energy can be dropped to the earth through the sample 21 and therefore, the grid 23b can be eliminated.

What is claimed is:

1. A scanning photoelectron microscope comprising:
   (a) a stage on which a sample is placed in a state in which gas is present around the sample;
   (b) a light source emitting light of a wavelength capable of causing photoelectrons to be emitted from the sample;
   (c) a condensing optical system for condensing the light from said light source on the sample;
   (d) a scanning system for scanning the sample and said light relative to each other; and
   (e) a detector capable of applying positive potential to the sample, and detecting photoelectrons created from the sample by said condensing, through said gas;
   said gas multiplying the photoelectrons from the sample.

2. A scanning photoelectron microscope according to claim 1, further comprising:
   (a) a sample chamber for containing the sample and said detector therein and keeping them air-tight to the surroundings;
   (b) a window for introducing said light into said sample chamber; and
   (c) a controller for controlling said sample chamber to a gas atmosphere of predetermined pressure.

3. A scanning photoelectron microscope according to claim 1, wherein said light is X-rays, and said scanning is effected by movement of said stage.

4. A scanning photoelectron microscope according to claim 1, further comprising:
   (a) a condensing lens system for condensing reflected light from the sample; and
   (b) a light receiving member for detecting the reflected light condensed by said condensing lens system.

5. A scanning photoelectron microscope comprising:
   (a) a stage on which a sample is placed in a state in which gas is present around the sample;
   (b) a light source emitting light of a wavelength capable of causing photoelectrons to be emitted from the sample;
   (c) a condensing optical system for condensing the light from said light source on the sample;
   (d) a scanning system for scanning the sample and said light relative to each other;
   (e) an electron energy selecting device for selecting only those of the photoelectrons emitted from the sample which have predetermined energy;
   (f) a detector capable of imparting positive potential to the sample, and detecting the photoelectrons selected by said electron energy selecting device, through said gas, said gas multiplying the photoelectrons from the sample; and (g) a sample chamber capable of containing the sample, said electron energy selecting device and said detector therein so as to keep them air-tight to the surroundings, and introducing said light onto the sample.

6. A scanning photoelectron microscope according to claim 5, wherein when the ionization and excitation cross section of said gas by electrons is $\sigma$ and the molecule density of said gas is N, said electron energy selecting device is disposed at a location within a value L from the sample toward the optical axis of said condensing optical system, where L satisfies the following equation:

$$L=1/(N\cdot\sigma).$$

7. A scanning photoelectron microscope according to claim 6, further comprising a controller for controlling said sample chamber to a gas atmosphere of predetermined pressure.

8. A scanning photoelectron microscope according to claim 7, wherein said controller renders said sample chamber into a helium atmosphere of predetermined pressure.

9. A scanning photoelectron microscope according to claim 7, wherein said controller renders said sample chamber into a nitrogen atmosphere of predetermined pressure.

10. A scanning photoelectron microscope according to claim 6, wherein said light is X-rays, and said scanning is executed by movement of said stage.

11. A scanning photoelectron microscope according to claim 5, further including a controller for controlling said sample chamber to a gas atmosphere of predetermined pressure.

12. A scanning photoelectron microscope according to claim 11, wherein said controller renders said sample chamber into a helium atmosphere of predetermined pressure.

13. A scanning photoelectron microscope according to claim 11, wherein said controller renders said sample chamber into a nitrogen atmosphere of predetermined pressure.

14. A scanning photoelectron microscope according to claim 5, wherein said light is X-rays, and said scanning is executed by movement of said stage.

15. A scanning photoelectron microscope comprising:

(a) a sample chamber for containing a sample in a state in which gas is present around the sample;

(b) an irradiation system which causes photoelectrons to be emitted from the sample; and (c) a detector which detects photoelectrons emitted from the sample and multiplied by the gas.

16. A microscope according to claim 15, wherein said irradiation system includes a device which causes X-rays to be converged on the sample.

17. A microscope according to claim 15, further comprising:

a device which adjusts a pressure within said chamber.

18. A scanning photoelectron microscope comprising:

(a) a system which irradiates a sample so as to produce photoelectrons from the sample; and (b) a detection system which detects photoelectrons produced by the sample through a gas which multiplies the photo-electrons.

19. A microscope according to claim 18, further comprising:

an optical device which detects reflected radiation from the sample.

20. A microscope according to claim 19, further comprising:

a system which displays at least one of a photoelectron image of the sample obtained by said detection system and an optical image of the sample obtained by said optical device.

* * * * *